US000001453H

United States Statutory Invention Registration [19]

[11] Reg. Number: H1453

[43] Published: Jun. 6, 1995

Yamano et al.

[54] N-ACETYL-D-GLUCOSAMINE DEACETYLASE AND A PROCESS FOR PREPARING THE SAME

[76] Inventors: Naoko Yamano, 9-1-803, Hirano Nishi 3-chome, Hirano-ku, Osaka-shi, Osaka-fu; Shizu Fujishima, 10-5-203, Tateishicho, Ikeda-shi, Osaka-fu; Ryutarou Tanaka, 4-15-306, Tagawa 3-chome, Yodogawa-ku, Osaka-shi, Osaka-fu, all of Japan

[21] Appl. No.: 154,350

[22] Filed: Nov. 18, 1993

[30] Foreign Application Priority Data

Mar. 12, 1993 [JP] Japan ..... 5-078653

[51] Int. Cl.[6] ..... C12N 9/78; C12N 9/80; C12P 21/04

[52] U.S. Cl. ..... 435/227; 435/71.1; 435/71.2; 435/84; 435/228; 435/231; 435/252.1

[58] Field of Search ..... 435/252.1, 227, 228, 435/231, 84, 71.1, 71.2

[56] References Cited

U.S. PATENT DOCUMENTS 5,252,468 10/1993 Fujishima et al. .

OTHER PUBLICATIONS

Asahi Garasu Kogyo Gijutsu Shoreikai Kenkyu Hokoku, 1992, 41, 299–304 (Japan); Chemical Abstracts, 99:84876v.

Bergey's Manual of Systematic Bacteriology, vol. 1, 518 (1957).

Can. J. Microbiol., vol. 31, 711–720 (1985).

*Primary Examiner*—Shean Wu

[57] ABSTRACT

There are provided N-acetyl-D-glucosamine deacetylase capable of hydrolyzing acetamide group of N-acetyl-D-glucosamine to produce D-glucosamine and acetic acid, which has the following physicochemical properties:

(1) Substrate specificity: N-acetyl-D-glucosamine monomer, not the oligomer or polymer thereof;
(2) Optimal pH: 7.8–8.2 at 37° C.;
(3) Stable pH: 6.0–9.0 at 45° C.;
(4) Optimal temperature: 28°–39° C.;
(5) Molecular weight: 70,000–200,000 as determined using TSK-gel G-3000 SW column, and a process for preparing the same using a microorganism belonging to Vibrio sp.

2 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

N-ACETYL-D-GLUCOSAMINE DEACETYLASE AND A PROCESS FOR PREPARING THE SAME

BACKGROUND OF THE INVENTION

1. Field of the Invention

The present invention relates to an enzyme N-acetyl-D-glucosamine deacetylase capable of hydrolyzing the acetamide group of N-acetyl-D-glucosamine to produce D-glucosamine and acetic acid. More particularly, the present invention relates to a deacetylase which acts specifically on the monomer of N-acetyl-D-glucosamine, and not on the oligomers including dimer and the polymer.

The present invention also relates to a process for preparing the above described enzyme, and to a process for hydrolyzing said acetamido group using the deacetylase of the present invention.

2. Description of the Prior Art

D-glucosamine, the deacetylated product of N-acetyl-D-glucosamine, is useful as pharmaceuticals, foodstuffs, and intermediates for the preparation of pharmaceuticals. In addition, oligosaccharides consisting of D-glucosamine unit have increasingly been drawing attention and becoming important as having valuable physiological activities such as antibacterial, antifungal and antitumor activities.

D-glucosamine has hitherto been prepared from N-acetyl-D-glucosamine which is prepared from purified chitin ($\beta$-1,4-poly-N-acetyl-D-glucosamine, obtained from the cuticle (crust) of a crustacean such as prawn or crab by removing inorganic salts, proteins and lipids), by deacetylating with a conc. alkali or mineral acid.

However, the hydrolysis of the N-acetyl group of N-acetyl-D-glucosamine does not progress so easily and therefore, relatively hard reaction conditions are necessary to complete the hydrolysis, for example, heating for a long period of time in a concentrated acid or alkali such as 30–60% solution, leading to an increase in the formation of undesirable by-products, and the yield of the desired D-glucosamine is low. Moreover, the elimination of the acid or alkali used necessitates additional elaboration and expense.

There have been a need for developping more mild methods of deacetylating N-acetyl-D-glucosamine in a high yield without the formation of undesirable by-products, and a biological method using an enzyme capable of deacetylating N-acetyl-D-glucosamine has been investigated.

As biological deacetylation methods, there have been several references known wherein microorganisms belonging to Mucor sp, Aeromonas sp. or Colletotrium sp. are used.

In a method using a microorganism belonging to Mucor sp., soluble glycol chitin and the pentamer are deacetylated to the extent of 12–14%, but there is no disclosure of a deacetylase acting only on the monomer of N-acetyl-D-glucosamine [Y. Araki, E. Ito, Biochem. Biophys. Res. Commun., 56: 669 (1974); Eur. J. Biochem., 55:71 (1975); Methods Enzymol., 161:510 (1988); L. L. Davis, S. Bartnicki-Garcia, Biochemistry, 23: 1065 (1984); C. Calvo-Mendez, J. Ruiz-Herrera, Exp. Mycol., 1:128 (1987)].

A method using a microorganism belonging to Aeromonas sp. intends to deacetylate solid chitin of high polymerization degree, and there is no disclosure of deacetylating monosaccharide [K. Shimahara, H. Iwasaki, Asahi Garasu Kogyo Gijutsu Shoreikai, 41: 299 (1982), C.A. 99:84876v (1983)].

There is no disclosure also of deacetylating monosaccharide using a microorganism belonging to Colletotrium sp. [H. Kauss, W. Jeblick, D. H. Young, Plant Sci. Lett. 28: 231 (1983); H. Kauss, B. Bauch, Methods in Enzymology, 161: 518 (1988)].

It has now surprisingly been found that a marine microorganism belonging to Vibrio sp. produces an enzyme which is capable of splitting the acetyl group of N-acetyl-D-glucosamine and which specifically acts on the monomer of N-acetyl-D-glucosamine and not on the oligomer or polymer thereof.

The enzyme as described above having such novel substrate specificity has never been known hitherto, and represents a useful functional enzyme.

SUMMARY OF THE INVENTION

Thus the present invention relates to a novel enzyme N-acetyl-D-glucosamine deacetylase capable of hydrolyzing acetamide group of N-acetyl-D-glucosamine to produce D-glucosamine and acetic acid. More particularly, the present invention relates to N-acetyl-D-glucosamine deacetylase which has the following physicochemical properties:

(1) Substrate specificity: N-acetyl-D-glucosamine monomer, not the oligomer or polymer thereof;
(2) Optimal pH: 7.8–8.2 at 37° C.;
(3) Stable pH: 6.0–9.0 at 45° C.;
(4) Optimal temperature: 28°–39° C.;
(5) Molecular weight: 70,000–200,000 as determined using TSK-gel G-3000 SW column.

More particularly, the present invention relates to N-acetyl-D-glucosamine deacetylase as defined above, which has a molecular weight of 80,000–150,000 as determined using TSK-gel G-3000 SW column.

Furthermore, the present invention relates to N-acetyl-D-glucosamine deacetylase as described above, which is obtained from a microorganism belonging to Vibrio sp., preferably from *Vibrio cholerae* non-01 (IFO 15429 ).

The present invention also relates to a process for preparing N-acetyl-D-glucosamine deacetylase as mentioned above, by incubating a microorganism belonging to Vibrio sp. capable of producing said deacetylase in an induction medium, and isolating said deacetylase from cells separated from said medium.

This invention further relates to a process as described above wherein the microorganism is previously incubated in a nutrition medium.

This invention also relates to a process as described above wherein the microorganism is *Vibrio cholerae* non-01 (IFO 15429).

The present invention also relates to a process for hydrolyzing acetamido group of N-acetyl-D-glucosamine monomer using the deacetylase of the present invention.

PREFERRED EMBODIMENT OF THE INVENTION

The physico-chemical properties of the enzyme of the present invention are described in detail hereinafter.

1) Action and substrate specificity

Acts on the acetamide group of N-acetyl-D-glucosamine and hydrolyzes the latter to D-glucosamine and acetic acid, and substantially does not affect the oligomers including dimer of N-acetyl-D-glucosamine.

2) Optimal pH and stable pH

The optimal pH of the enzyme of the present invention varies widely depending on the origin of the microorganism used to produce the enzyme, but usually in the range of about 4.0–9.0. For example, the optimal pH of the enzyme derived from Vibrio sp. is in the range of 7.8–8.2 as determined colorimetrically according to indole-HCl method at pH 5.6–10.8. The buffer solution used at pH 5.6–6.0 is 100 mM $CH_3COOH$—$CH_3COONa$, at pH 6.0–9.0, 100 mM $KH_2HPO_4$–$Na_2HPO_4$ is used, and at pH 9.6–10.8, 200 mM $Na_2HPO_4$-NaOH is used.

Figure 1:
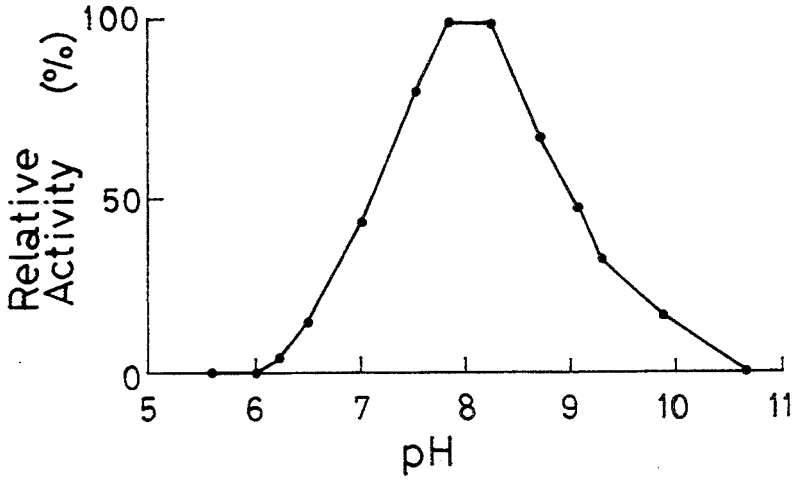
FIG. 1 shows the relationship between the relative activity (%) of N-acetyl-D-glucosamine deacetylase of the present invention and the pH value, at 37° C.

The relative activity of the enzyme obtained from Vibrio sp. is shown in FIG. 1.

Figure 3:
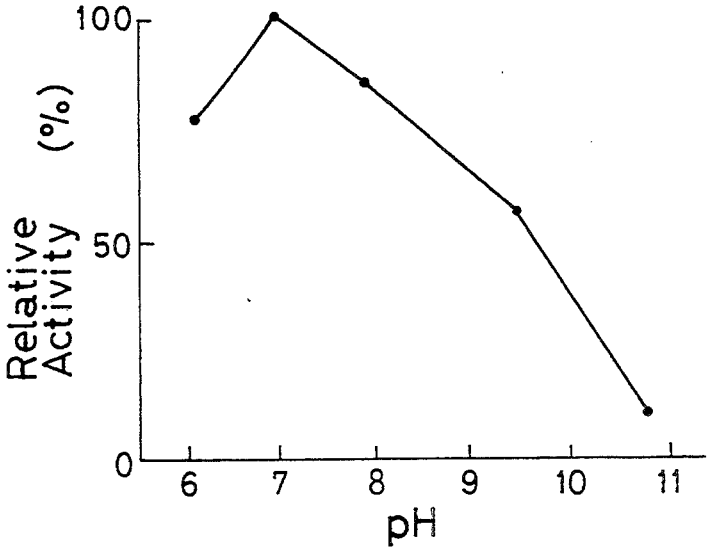
FIG. 3 shows the relationship between the relative activity (%) of the N-acetyl-D-glucosamine deacetylase of the present invention and the pH value, at 37° C., after incubation at 45° C. for a period of 30 minutes.
Figure 4:
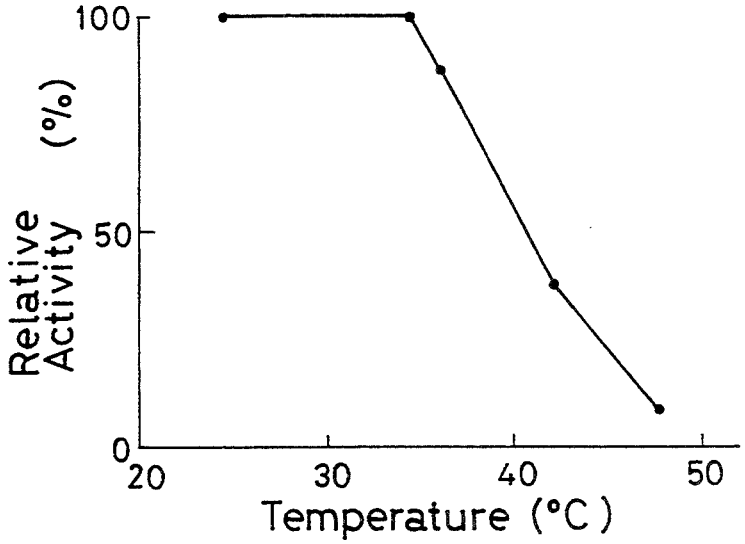
FIG. 4 shows the relationship between the relative activity (%) of the N-acetyl-D-glucosamine deacetylase of the present invention and the temperature (°C.), after incubation at pH 7.8 at a given temperature for a period of 30 minutes.

The stable pH wherein not less than 50% of the initial activity of the enzyme is retained, as determined at 37° C. after incubation in a given buffer at 45° C. for 30 minutes, varies depending on the origin of the microorganism used to produce the enzyme, but usually ranges from about 3.0 to 9.0. For example, the stable pH of the enzyme derived from Vibrio sp. is in the range of about 6.0–9.0. The relative activity after such incubation of the enzyme obtained from Vibrio sp. is shown in FIG. 3.

3) Optimal temperature range

Figure 2:
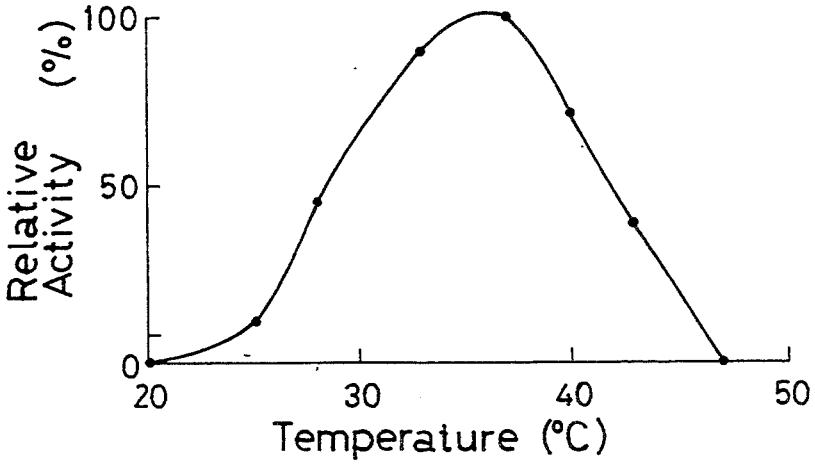
FIG. 2 shows the relationship between the relative activity (%) of N-acetyl-D-glucosamine deacetylase of the present invention and the temperature (°C.), at pH 7.8.

The optimal temperature for the enzymatic activity varies widely depending on the origin of the microorganism used to produce the enzyme, but usually ranges from about 10° C. to 50° C. For example, the optimal temperature of the enzyme obtained from Vibrio sp. as determined at 20°–47° C. is in the range of about 28°–39° C. The relative activity of the enzyme derived from Vibrio sp. is shown in FIG. 2.

4) Molecular weight

The molecular weight of the enzyme of the present invention as determined by TSK-gel G-3000 SW column is 70,000–200,000. The molecular weight of the enzyme derived from Vibrio sp. is 80,000–150,000.

N-acetyl-D-glucosamine deacetylase of the present invention can be obtained by incubating a microorganism belonging to Vibrio sp. Namely, a microorganism belonging to Vibrio sp. is incubated in a medium containing an inducer. Suitable inducers include chitin, chitin hydrolysate, N-acetyl-D-glucosamine, N-acetyl-D-glucosamine oligomers. These inducers can be used alone or in combination thereof. Inducers are used in a concentration of about 0.1 g/L or above, preferably at 1.0–50 g/L.

The present invention is further described in detail referring to the production of the enzyme from a microorganism *Vibrio cholerae* non-01 (IFO 15429). The Vibrio sp. microorganisms are publicly known. Among them, *Vibrio cholerae* non-01 (IFO 15429) was deposited to INSTITUTE FOR FERMENTATION, OSAKA (IFO), 17–85, Jusohonmachi 2-chome, Yodogawa-ku, Osaka 532, Japan, under the accession number IFO 15429. The bacteriological properties of *Vibrio cholerae* non-01 (IFO 15429) are shown in Can. J. Microbiol., Vol.31, 711–720 (1985) and Bergey's Mannual of Systematic Bacteriology Vol. 1, 518 (1957). In Bergey's Mannual of Systematic Bacteriology, *Vibrio Pacini* corresponds to *Vibrio cholerae* non-01.

(1) Incubation conditions

The cells of a microorganism *Vibrio cholerae* non-01 (IFO 15429) is at first incubated in a conventional nutrition medium which need not specifically defined. For example, such conventional medium contains glucose, maltose, xylose, sucrose, etc., as a carbon source, yeast extract, peptone, meat extract, organic nitrogen sources such as aminoacid, inorganic nitrogen sources such as ammonium sulfate, ammonium chloride, etc., as a nitrogen source, magnesium sulfate, magnesium chloride, sodium phosphate, potassium phosphate, potassium chloride, sodium chloride, calcium chloride, etc., as a mineral source, in an appropriate combinations. The pH of the medium is adjusted between 6.5–8.0 by the addition of an appropriate acid or base, and the medium is autoclaved. Incubation is conducted aerobically at 25°–40° C., preferably at 37°C., for 5–24 hours with stirring or o agitation. The cells from the culture as incubated above is used for the production of N-acetyl-D-glucosamine deacetylase of the present invention by incubating said cells in an induction medium containing an inducer in addition to a carbon source, a nitrogen source and a mineral source.

For example, an induction medium contains 3 g of ammonium nitrate, 1 g of dipotassium hydrogen phosphate, 20 g of sodium choloride, 0.5 g of magnesium sulfate, 0.08 g of calcium chloride, 50 g of N-acetyl-D-glucosamine in 1 L of the medium of pH 7.4.

*Vibrio cholerae* non-01 (IFO 15429) is aerobically incubated at 25°–40° C., preferably at 37°C. for 1–3 days while stirring or agitating.

(2) Isolation of the enzyme

The enzyme of the present invention can be recovered and purified from the culture using one or more conventional methods. For example, the culture thus incubated is centrifuged to collect cells, and the cells are disrupted by sonication, to give cell extract. The extract is purifed using ion exchange chromatography, adsorption chromatography, gel filtration chromatography, etc. A purification procedure comprises, for example, the following steps:

(1) the cells are disrupted by the treatment with supersonic waves and centrifuged to give cell-free extract;

(2) The cell-free extract is subjected to DEAE Bio-Gel chromatography and eluted with 10 mM phosphate buffer containing 150 mM NaCl;

(3) subjected further to hydroxyapatite column chromatography and eluted with 50 mM phosphate buffer; and (4) subjected to HPLC using TSK-gel 3000 SW gel-filtration colomn.

The enrichment degree of the enzyme at each purification step is shown in Table 1 below, wherein the activity is determined by the method as described hereinafter.

TABLE 1

| Puri. Step | Tot. Prot. mg | Tot. Act. Unit | Spec. Act. Unit/mg | Enrich. Degree | Recov. % |
|---|---|---|---|---|---|
| (1) | 1730 | 6.20 | 0.00358 | 1 | 100 |
| (2) | 68.6 | 6.00 | 0.0875 | 24.4 | 96.7 |
| (3) | 6.57 | 2.45 | 0.373 | 104 | 39.5 |
| (4) | 0.72 | 0.88 | 1.22 | 346 | 14.2 |

As evident from Table 1, after the purification step (4), an enzyme having specific activity of 1.22 unit/mg protein (enriched 346-fold the activity of the initial value) can be obtained. Using this enzyme, enzymatic characteristics as described hereinafter is investigated.

(3) The determination of the enzymatic activity

An enzyme solution (0.1 ml) is added to 0.3 ml of 100 mM phosphate buffer (pH 7.8) containing 0.1 ml of 1% N-acetyl-D-glucosamine as a substrate, and the resultant mixture is incubated at 37° C. for 30 minutes. The amount of D-glucosamine formed is determined colorimetrically using indole-HCl according to the method of Z. Dische and E. Borenfreund [J. Biol. Chem., 184:517 (1950)]. One unit of the enzyme is defined as the amount of the enzyme which is capable of producing 1 μmol D-glucosamine from N-acetyl-D-glucosamine per minute at 37° C.

As described above, N-acetyl-D-glucosamine deacetylase of the present invention is a novel enzyme which has not been known hitherto and which enables to deacetylate monomeric N-acetyl-D-glucosamine in a mild condition to produce D-glucosamine. It is possible from the substrate specificity of this enzyme to deacetylate only monomeric N-acetyl-D-glucosamine, among the mixture thereof with oligomers. The deacetylated product D-glucosamine is useful as a starting material for the preparation of many pharmaceuticals, functional oligosaccharides, etc., and has a wide range of utility.

The present invention is further illustrated by the following EXAMPLE.

EXAMPLE

1. Incubation of *Vibrio cholerae* non-01 strain (IFO 15429 )

*Vibrio cholerae* non-01 strain (IFO 15429) was incubated in a plate agar medium containing 0.6 g of ammonium nitrate, 0.2 g of dipotassium hydrogen phosphate, 2 g of sodium chloride, 0.12 g of magnesium sulfate, 0.02 g of calcium chloride, 10 g of glucose and 3 g of agar per 200ml of the medium of pH 7.4 at 37°C. for 24 hours, and the cells were collected using a spatula. The cells thus obtained were then aerobically incubated with shaking for 24 hours in the following induction medium. Induction medium: 1.5 g of ammonium nitrate, 0.5 g of dipotassium hydrogen phosphate, 10 g of sodium chloride, 0.3 g of magnesium sulfate, 0.04 g of calcium chloride, and 25 g of N-acetyl-D-glucosamine in 500 ml of a liquid medium of pH 7.4.

2. Recovery and purification of the enzyme

The culture thus obtained was cetrifuged at 8000 g for 20 minutes to afford 11 g of wet cells. The cells were suspended in 40ml of physiological saline and sonicated at 0° C. for 10 minutes (20 seconds operations at intervals of 20 seconds), then centrifuged to give cell-free extract containing 1.73 g of a protein having specific activity of 0.00358 unit/mg protein.

The cell-free extract as obtained above was applied to a column charged with DEAE Bio-Gel A which had been equilibrated with 0.01M phosphate buffer (pH 7.0), and eluted with a stepwise NaCl gradient eluent. Using 150 mM NaCl, 68.6 mg of a protein having specific activity of 0.0875 U/mg protein was eluted. The eluate was further applied to a hydroxyapatite column and eluted with a stepwise gradient phosphate buffer. 10 ml of an eluate containing 2.45 mg of a protein having specific activity of 0.373 U/mg protein was eluted using 50 mM phosphate buffer.

The eluate (10 ml) thus obtained was concentrated to 0.4ml by ultrafiltration (exclusion limit 100,000) and subjected to HPLC using TSK gel 3000 SW column to give 0.72 mg of purified enzyme having specific activity of 1.22 U/mg protein. The enrichment degree of the activity was 346-fold of the initial value and the recovery of the enzyme was 14.2%. The molecular weight of this enzyme was 80,000–150,000.

3. Substrate specificity of the enzyme

The substrate specificity of the enzyme as obtained above was investigated using monomer and several oligomers (2–6 mers) of N-acetyl-D-glucosamine (SEIKAGAKU KOGYO CO. LTD. Japan), and chitin as a substrate. These substrates were added at a concentration of 0.2%, and the enzymatic reaction was allowed to take place at a temperature of 37° C. and a pH of 7.8 for one hour. The amount of D-glucosamine formed was determined using indole-HCl according to the method of Z. Dische and E. Borenfreund [J. Biol. Chem., 184: 517 (1950)]. The results obtained are shown in Table 2 below.

TABLE 2

| Substrate | Enzymatic Activity Unit/mg | Relative Activity % |
|---|---|---|
| GlcNAc | 1.22 | 100 |
| $(GlcNAc)_2$ | N.D. | — |
| $(GlcNAc)_3$ | N.D. | — |
| $(GlcNAc)_4$ | N.D. | — |
| $(GlcNAc)_5$ | N.D. | — |
| $(GlcNAc)_6$ | N.D. | — |
| Chitin | N.D. | — |

One unit of enzyme activity is defined as the amount of the enzyme required to form 1 μ equivalent of the amino group per min at 37° C..

As seen from Table 2 above, formation of D-glucosamine from monomeric N-acetyl-D-glucosamine can be observed while none of the oligomers tested (2-mer to 6-mer) and chitin show the formation of D-glucosamine.

What is claimed is:

1. N-acetyl-D-glycosamine deacetylase capable of hydrolyzing the acetamide group of N-acetyl-D-glycosamine to produce D-glycosamine and acetic acid, which is obtained from *Vibrio cholereae* non-01 (IFO 15429) and which has the following physicochemical properties:

substrate specificity: N-acetyl-D-glycosamine monomer;

optimal pH: 7.8–8.2 at 37° C.;

stable pH: 6.0–9.0 at 45° C.;

optimal temperature: 28°–39° C.; and molecular weight: 70,000–200,000.

2. N-acetyl-D-glucosamine deacetylase as claimed in claim 1 which has a molecular weight of 80,000–150,000.

* * * * *